(12) United States Patent
Calderon et al.

(10) Patent No.: US 7,217,236 B2
(45) Date of Patent: May 15, 2007

(54) UNIVERSAL PNEUMATIC VENTRICULAR ASSIST DEVICE

(75) Inventors: Moises Calderon, Huixguilucan (MX); Emilio Sacristan, Santa Ursula Xitla (MX)

(73) Assignee: Innovamedica S.A. de C.V., Alvaro Obregon (MX)

( * ) Notice: Subject to any disclaimer, the term of this patent is extended or adjusted under 35 U.S.C. 154(b) by 366 days.

(21) Appl. No.: 10/854,567

(22) Filed: May 25, 2004

(65) Prior Publication Data

US 2004/0242954 A1 Dec. 2, 2004

Related U.S. Application Data

(60) Provisional application No. 60/475,062, filed on May 30, 2003.

(51) Int. Cl.
*A61N 1/362* (2006.01)
(52) U.S. Cl. .................. 600/16; 623/3.1; 623/3.18; 623/3.21
(58) Field of Classification Search ............. 600/16; 623/3.1, 3.18, 3.21
See application file for complete search history.

(56) References Cited

U.S. PATENT DOCUMENTS

| 3,208,448 | A | 9/1965 | Woodward |
| 3,553,736 | A | 1/1971 | Kantrowitz et al. |
| 3,974,825 | A | 8/1976 | Normann |
| 4,008,710 | A | 2/1977 | Chmiel |
| 4,162,543 | A | 7/1979 | Shumakov et al. |
| 4,222,127 | A | 9/1980 | Donachy et al. |
| 4,573,997 | A | 3/1986 | Wisman et al. |
| 4,576,606 | A | 3/1986 | Pol et al. |
| 4,578,077 | A | 3/1986 | Joh |
| 4,704,120 | A | 11/1987 | Slonina |
| 4,723,948 | A | 2/1988 | Clark et al. |
| 4,781,715 | A | 11/1988 | Wurzel |
| 4,838,889 | A | 6/1989 | Kolff |
| 4,863,461 | A | 9/1989 | Jarvik |
| 4,902,291 | A | * 2/1990 | Kolff .................. 623/3.21 |
| 5,135,539 | A | 8/1992 | Carpentier |
| 5,300,113 | A | 4/1994 | Arpesella et al. |
| 5,332,403 | A | 7/1994 | Kolff |
| 5,348,528 | A | 9/1994 | Vince |
| 5,803,720 | A | * 9/1998 | Ohara et al. .............. 417/420 |

(Continued)

FOREIGN PATENT DOCUMENTS

WO WO 98/36792 8/1998

*Primary Examiner*—Robert E. Pezzuto
*Assistant Examiner*—Brian T. Gedeon
(74) *Attorney, Agent, or Firm*—Holland & Bonzagni, P.C.; Donald S. Holland, Esq.

(57) ABSTRACT

A pneumatic ventricular assist device (VAD) is disclosed for use in any circulatory support application including RVAD, LAVD, or BIVAD, trans-operative, short-term or long-term, tethered implantable or extracorporeal. In the preferred embodiment, the VAD consists of a soft contoured pump shell and a disposable pumping unit, which includes: a pump sac; an inlet and an outlet (a.k.a. discharge) with one-way valves; and tubing connectors. The valves comprise a cantilevered pair of closely adjacent thin ledges, nicknamed "valve leaflets," that resemble needle-nose pliers. The valve leaflets permit a one-way flow of blood between them, as an opposite flow pinches the distal ends of leaflets together, thereby closing off the channel between them. This design is specially designed to allow continuous and fluid movement of blood (in one direction) while limiting blood-contacting surfaces.

6 Claims, 7 Drawing Sheets

U.S. PATENT DOCUMENTS

| | | |
|---|---|---|
| 6,001,056 A | 12/1999 | Jassawalla et al. |
| 6,102,845 A | 8/2000 | Woodard et al. |
| 6,117,169 A | 9/2000 | Moe |
| 6,132,363 A | 10/2000 | Freed et al. |
| 6,146,325 A | 11/2000 | Lewis et al. |
| 6,155,610 A | 12/2000 | Godeau et al. |
| 6,165,215 A | 12/2000 | Rottenberg et al. |
| 6,174,331 B1 | 1/2001 | Moe et al. |
| 6,344,022 B1 | 2/2002 | Jarvik |
| 6,530,876 B1 | 3/2003 | Spence |
| 6,949,065 B2 * | 9/2005 | Sporer et al. ............ 600/16 |
| 2002/0072698 A1 | 6/2002 | Chiang et al. |
| 2003/0023131 A1 | 1/2003 | Antaki |

* cited by examiner

UNIVERSAL PNEUMATIC VENTRICULAR ASSIST DEVICE

This application claims priority from a Provisional Application, Ser. No. 60/475,062, filed May 30, 2003.

FIELD OF THE INVENTION

The present invention relates to blood pumping devices, and, more particularly, to ventricular assist devices.

BACKGROUND

A ventricular assist device ("VAD"is used to help supplement the heart's pumping action both during and after certain kinds of surgery, in situations where a complete cardiopulmonary bypass (using a heart-lung machine) is neither needed nor advisable in light of the serious side effects associated therewith. Ventricular assist devices typically comprise a pair of cannulae or other tubing and some sort of pump operably connected to the cannulae. In use, the cannulae are attached to either the left side of the heart (i.e., a left ventricular assist device, LVAD) or to the right side of the heart (i.e., a right ventricular assist device, RVAD) "in parallel" (i.e., the pump supplements the heart's pumping action but does not completely bypass it, and the pump is activated). Alternatively, a pump may be directly implanted into the body.

Originally, ventricular assist devices were air powered, wherein fluctuating air pressure, provided by a simple mechanical air pump machine, was applied to a bladder-like sac. The bladder had input and output valves, so that blood would enter the bladder through the input valve when the pressure on the bladder was low, and exit the bladder through the output valve when the pressure on the bladder was high. Unfortunately, these pneumatic ventricular assist devices were complicated, and used expensive mechanical valves that were prone to failure, subject to "clogging," and that caused blood trauma or damage because of hard, metal edges and the like.

To overcome these problems, other types of ventricular assist devices were developed, including axial flow pumps for temporary insertion directly into the heart, and centrifugal pumps. The former are based on the Archymides' Principle, where a rod with helical blades is rotated inside a tube to displace liquid. In use, a catheter-mounted, miniature axial flow pump is appropriately positioned inside the heart, and is caused to operate via some sort of external magnetic drive or other appropriate mechanism. With high enough RPM's, a significant amount of blood can be pumped. In the case of centrifugal pumps, blood is moved by the action of a rapidly rotating impeller (spinning cone or the like), which causes the blood to accelerate out an exit. Both of these categories of ventricular assist devices are generally reliable and implantable, but are very expensive, not particularly durable, and are not useful in situations where a patient needs a true pulsating blood supply. Specifically, axial and centrifugal pumps are typically left on in a continuous operation mode, where a steady stream of blood is supplied on a continuous basis, as opposed to the natural rhythm of the heart, which acts on a periodic, pulse-producing basis. In addition, such pumps are still largely in the developmental or trial phase.

Accordingly, a primary object of the present invention is to provide a simpler pneumatic ventricular assist device that offers the advantages of pneumatic operation without the drawbacks associated with prior pneumatic devices.

SUMMARY

A pneumatic ventricular assist device ("VAD") is disclosed for use in any circulatory support application including RVAD, LAVD, or BIVAD (i.e., bi-ventricular assist device), trans-operative, short-term or long-term, tethered implantable or extracorporeal. The preferred VAD comprises a soft-contoured (e.g., rounded, low-profile) split pump shell (i.e., casing) and a disposable pumping unit that includes an inflatable and collapsible blood sac, two one-way valves, and two tubing connectors. The pumping unit contains a uniquely designed, cantilevered pair of closely adjacent thin, tapered ledges (nicknamed "valve leaflets") that resemble needle-nose pliers. The ledges permit a one-way flow of blood between them, as an opposite flow pinches the ledges together, pushing the ledges together to close off the channel between them. This design allows continuous and fluid movement of blood (in one direction) while limiting blood-contacting surfaces. The components can be inexpensively and reliably manufactured by injection molding. Also, the design of the VAD, according to the present invention, facilitates priming, de-bubbling, and connection to the body.

For assembly, the split pump shell (e.g., two halves in a clam shell-like arrangement) is opened, the pumping unit is positioned inside, and the shell is closed. The interior of the shell is complementary in shape to the pumping unit: a pump chamber portion holds the blood sac; and a pump inlet and a pump outlet (a.k.a. discharge), both shaped to securely hold the valves and tubing connectors. A disposable seal rests between the two clamshell halves for sealing the connection there between.

In use, the presented VAD is connected to a patient's heart by way of two cannulae connected to the tubing connectors (i.e., the cannulae are connected to the heart at appropriate locations according to standard surgical practices). Then, a pneumatic drive unit is attached to an air inlet in the pump shell by way of an air line or the like. Subsequently, the drive unit is activated to cause the blood sac to move in and out (i.e., collapse and inflate), in a gentle pumping action, by way of controlled periodic air pressure introduced into the pump shell through the air inlet.

BRIEF DESCRIPTION OF THE DRAWINGS

These and other features, aspects, and advantages of the present invention will become better understood with respect to the following description, appended claims, and accompanying drawings, in which:

DETAILED DESCRIPTION

With reference to FIGS. 1–7, a preferred ventricular assist device (VAD), constructed in accordance with the invention, is disclosed. VAD 10 includes: a reusable pump shell 12 having a first or upper "clamshell" half 14 and a second or lower clamshell half 16 removably attachable to the first half 14; a disposable seal 18 that fits between the two pump shell halves 14, 16; and a disposable pumping unit 20 that includes: a disposable blood sac 22 that fits in the pump shell 12; two disposable, unique one-way injection-molded valves 24, 26 connected in fluid communication with the blood sac 22; and two tubing connectors 28, 30 attached to the valves. Although the preferred valves 24, 26 are identical, one valve 26 is positioned to act as an inlet valve, and the other valve 24 (shown in FIGS. 4A, 4B) is positioned to act as an outlet valve (i.e., blood can only flow through the valves 24, 26 as indicated by the arrows in FIG. 3).

For assembly, the disposable pumping unit 20 is placed against the lower pump shell half 16, the seal 18 is positioned in place, and the upper pump shell half 14 is placed against and connected to the lower pump shell half 16 (by way of screws or other fasteners). In use, the ventricular assist device 10 is appropriately connected to a patient's heart by way of a ventricular (or atrial) cannula 32 and an arterial cannula 34 respectively connected to the tubing connectors 28, 30. Then, a pneumatic drive unit 36 is operably attached to an air inlet 38 in the ventricular assist device 10 by a pneumatic line 40 or the like (see FIG. 7). Subsequently, the drive unit 36 is activated to cause a portion of the disposable blood sac 22 to move in and out, in a gentle pumping action, by way of controlled fluctuating air pressure introduced into the pump shell 12 through the air inlet 38.

Figure 1:
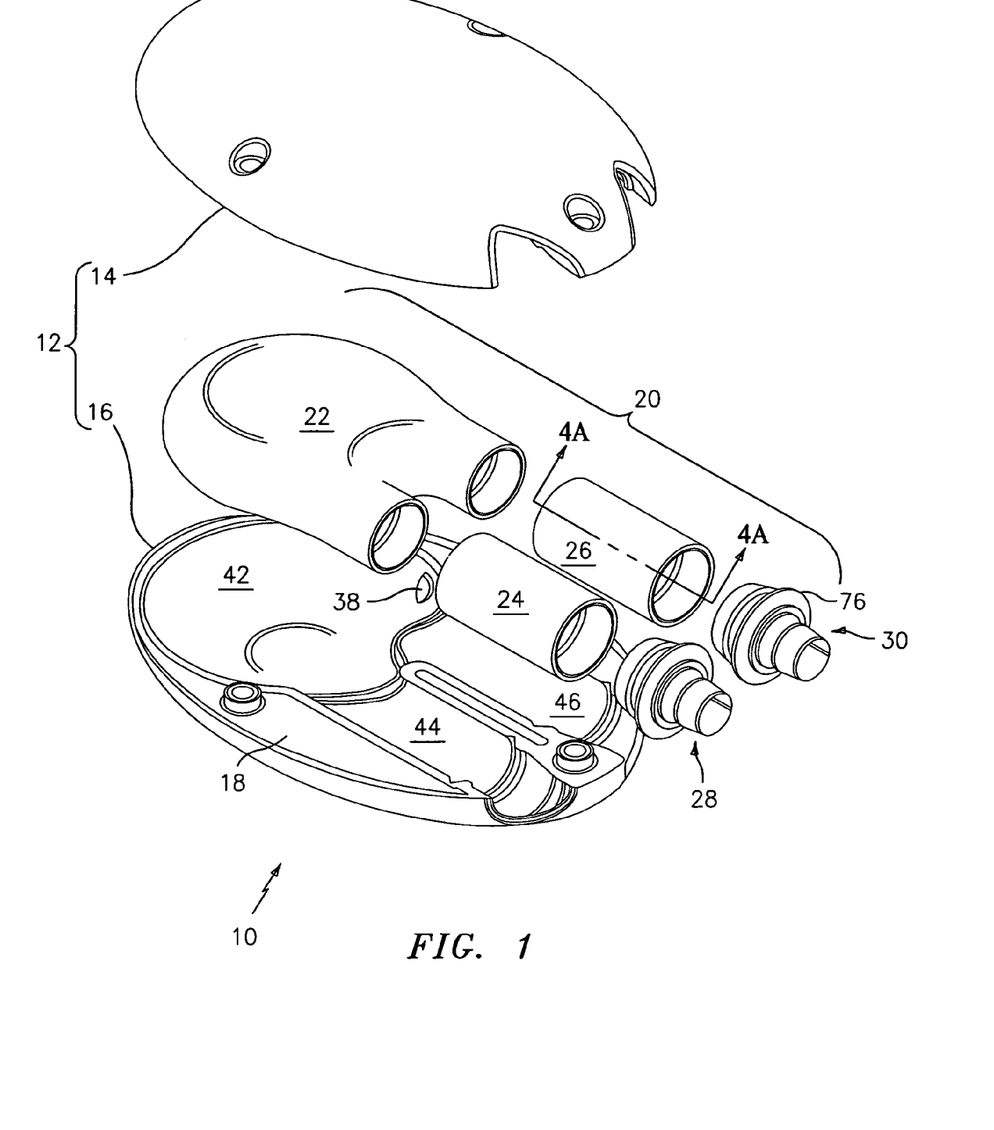
FIG. 1 is a perspective exploded view of a universal pneumatic ventricular assist device according to the present invention.
Figure 2:
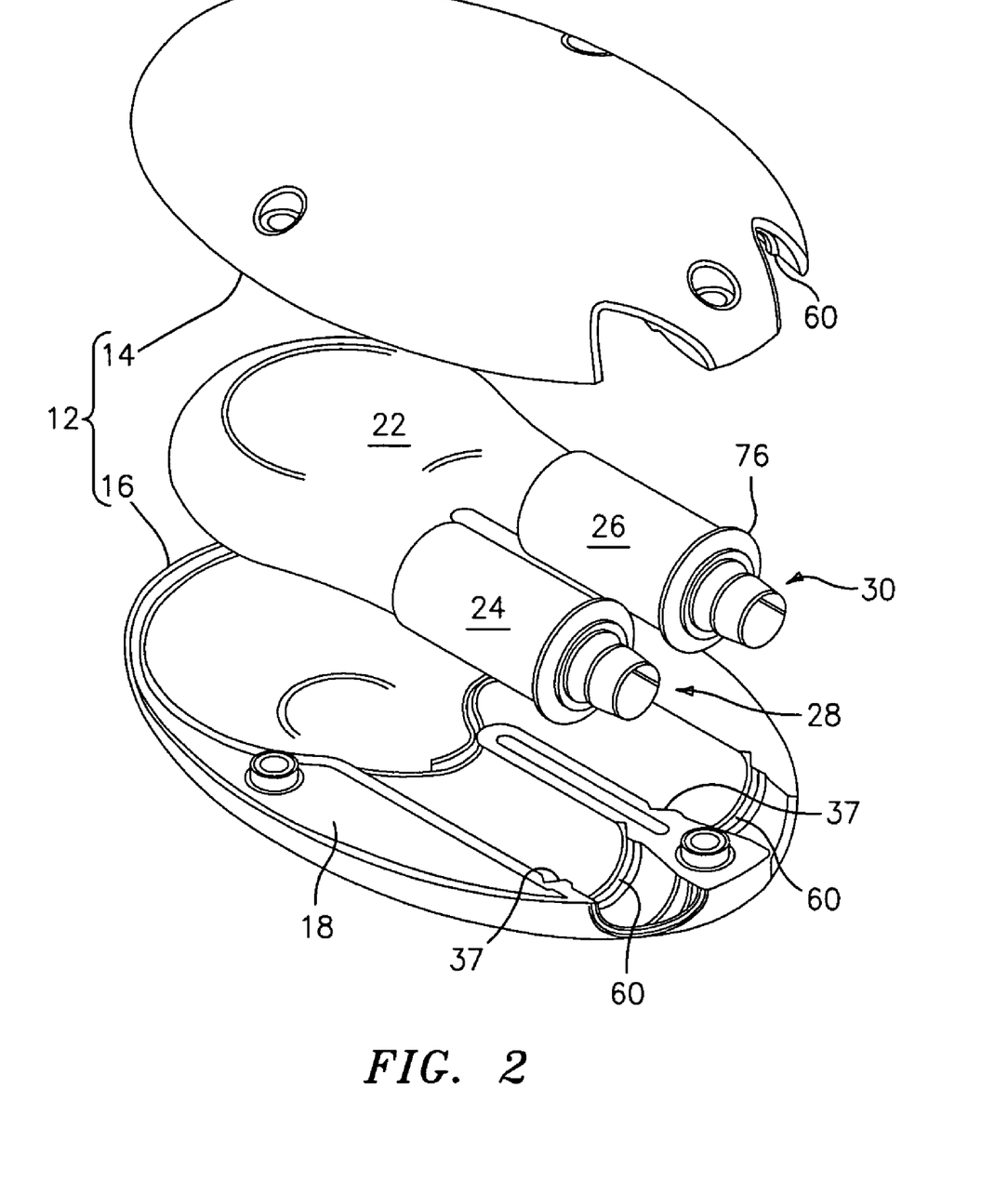
FIG. 2 is a perspective exploded view of the ventricular assist device with an assembled disposable pump assembly.
Figure 3:
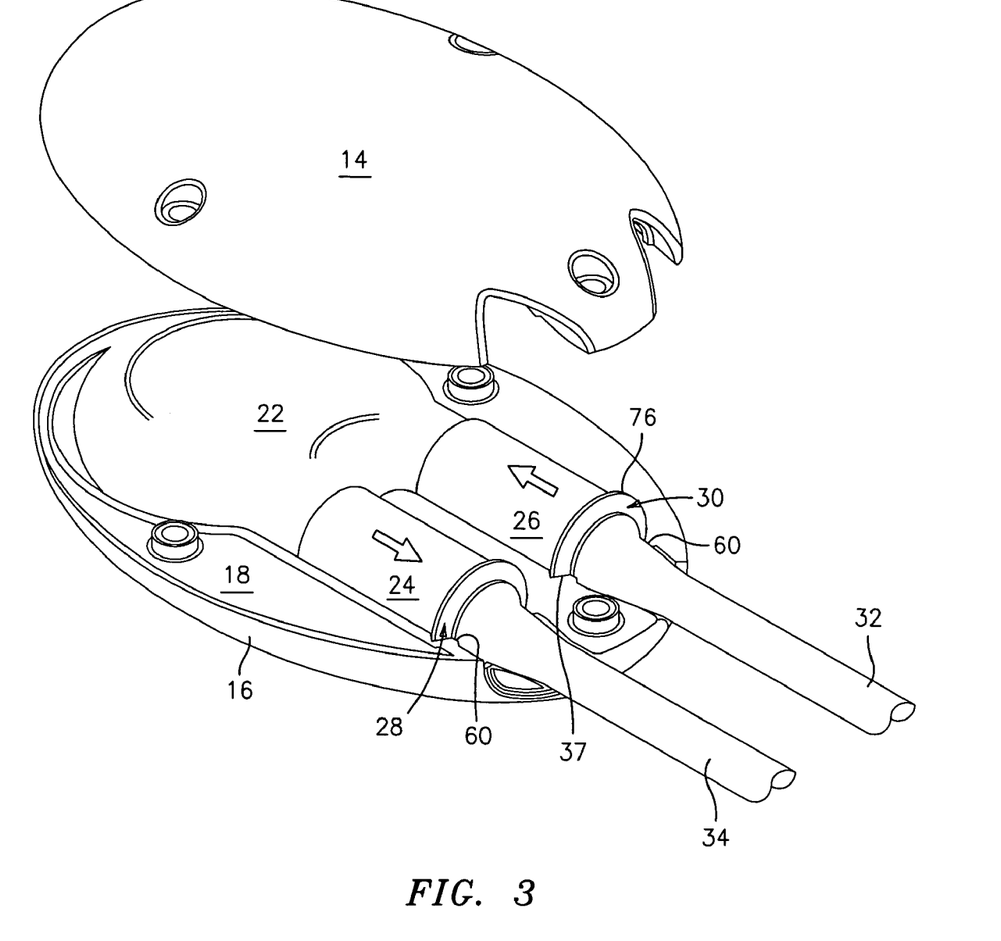
FIG. 3 is a perspective, partially exploded view of the ventricular assist device in place against a lower half of a pump shell portion of the ventricular assist device.

The pump shell 12 is either molded or machined from a hard material that may or may not be implantable in the human body, and may or may not be reusable. The pump shell 12 comprises the two halves 14, 16 (generally similar to one another), which mate together like a clamshell and together define a rounded interior, pump chamber 42 a generally cylindrical pump inlet 44, and a generally cylindrical pump outlet 46. As best seen in FIGS. 2 and 3, the pump inlets 44, 46 are provided with annular contours or shoulders (e.g., 37) for holding the connectors 28, 30 (i.e., each pump shell half includes a semi-annular shoulder which, when the two halves are connected, together define an annular shoulder). In addition, the lower shell half 16 includes the air inlet 38, which is a small hole or channel extending from the outer surface of the shell through the shell wall to the pump chamber 42. The outer surfaces of the shell halves 14, 16 are rounded, while the peripheral inner surfaces are flat so that the shell halves fit snugly against one another. The shape of the pump shell is generally flat and softly contoured (i.e., rounded, ellipsoidal) so that it may be comfortably implanted.

As mentioned, the pump inlet and outlet 44, 46 are generally cylindrical and dimensioned to hold and support the entireties of the cylindrical valves 24, 26 therein. As should be appreciated, having the valves enclosed within the confines of the complementary-shaped pump inlet and outlet maximize support of the valves, thereby enhancing their performance and durability. It also reduces the likelihood of the valves becoming dislodged or loose during use.

Figure 4A:
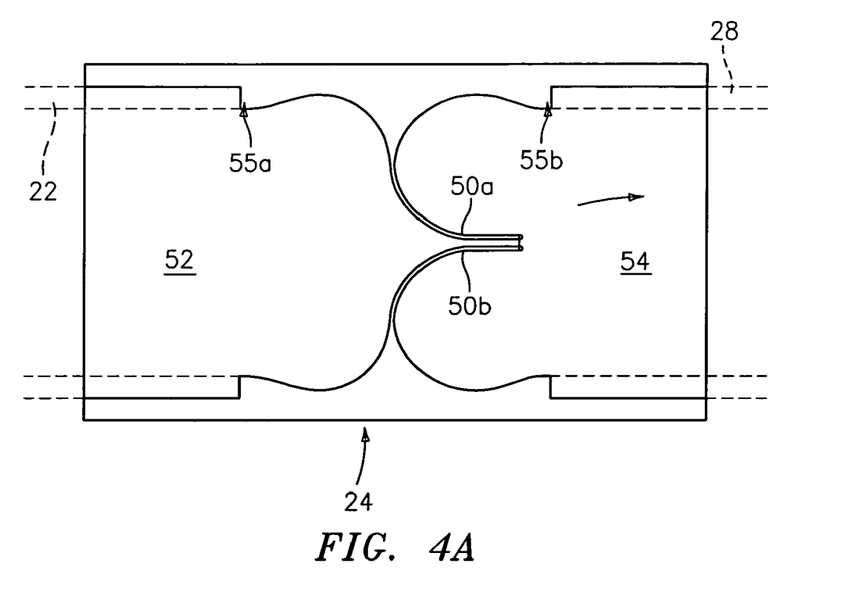
FIG. 4A is a elevation cross-sectional view of a valve portion of the ventricular assist device, taken along line 4A—4A in FIG. 1.
Figure 4B:
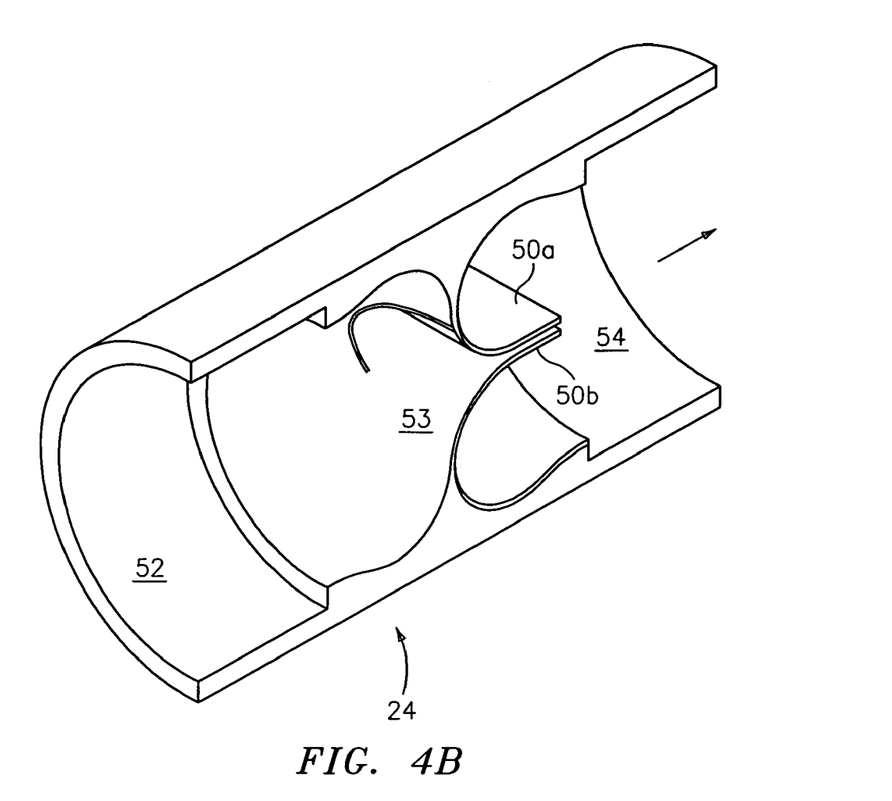
FIG. 4B is a perspective cross-sectional view of the valve portion of the ventricular assist device shown in FIG. 4A.

The blood sac 22, valves 24, 26, and cannulae 32, 34 are specially designed to allow continuous and fluid motion of blood and to limit blood contacting surfaces. These components are made of a supple elastomer such as silicone that will stretch and deform to pressure gradients reducing the damage to blood cells. With reference to FIGS. 4A and 4B, the valves 24, 26 are hinge-less and have valve leaflet portions 50a, 50b that are flexible and elastic, simulating the action of natural heart valves, and improving their reliability and durability. The preferred valves are injection molded in four piece molds reducing the manufacturing cost compared to biological or mechanical valves. In use, blood can flow through the valves in one direction only, from the valve inlet 52 to the valve outlet 54, i.e., in the direction of the arrows in the figures. Specifically, when the pressure is greater on the valve inlet side 52, the valve leaflets 50a, 50b respectively flex upwards and downwards, allowing blood to pass. However, when the pressure is greater on the valve outlet side 54, the leaflets are gently but forcibly compressed together, preventing blood from flowing back through the valve. Because the valves are each one-piece, are made from silicone (or another suitable material), and have rounded or contoured inner surfaces, they are very reliable, perform well, and minimize damage to blood. For example, as shown in FIG. 4B, note that the valve wall 53a, 50b leading up to the leaflets 50a, 50b is rounded/sloped to minimize blood disturbance.

In other words, the valve leaflets 50a, 50b are a cantilevered pair of closely adjacent thin ledges that resemble the head of needle-nose pliers. Each pair of leaflets defines a channel, between the pair, that is normally open (i.e., from end to end) in the absence of any compressive force pushing against the outside of the ledges. The leaflets permit a one-way flow of blood in the channel formed between them. The distal ends of the leaflets bias slightly outwardly, away from each other, as blood flows through the channel in the desired direction. An opposite blood flow, however, acts as compressive force and pinches the distal ends of the leaflets together, thereby closing off the channel between them. During use of the VAD 10, a channel in one of the one-way valves is open, while the channel in the channel in the other one-way valve is pinched closed.

As indicated in FIG. 4A, the sac 22 and connectors 28 are configured to fit within the entrance and exit ends of the valves 24, 26 and against interior, circumferential shoulders 55a, 50b provided in the valves. This produces a continuous surface between the various elements and eliminates any sharp lips or ridges in the blood flow path, reducing blood damage.

Figure 5A:
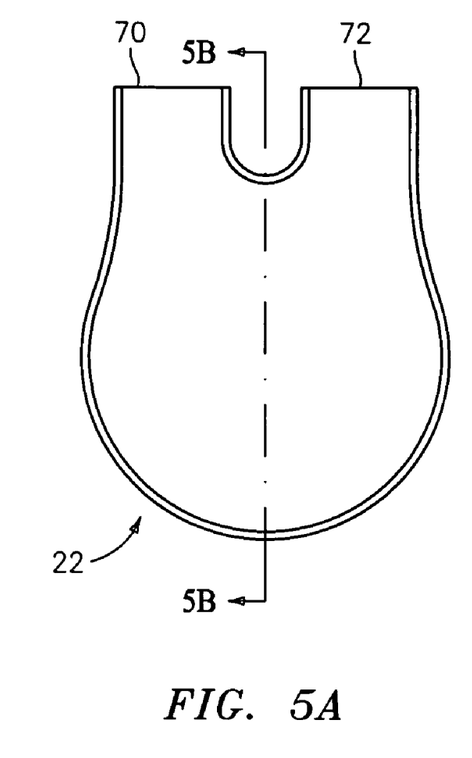
FIG. 5A is a plan view of a disposable pump blood sac portion of the ventricular assist device.
Figure 5B:
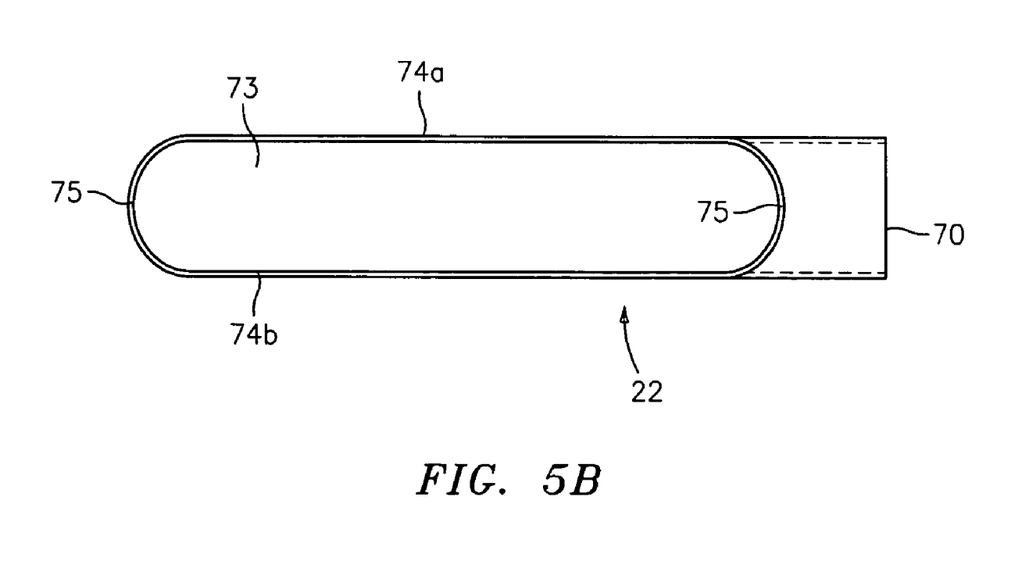
FIG. 5B is a cross-sectional view of the disposable blood sac taken along line 5B—5B in FIG. 5A.
Figure 6A:
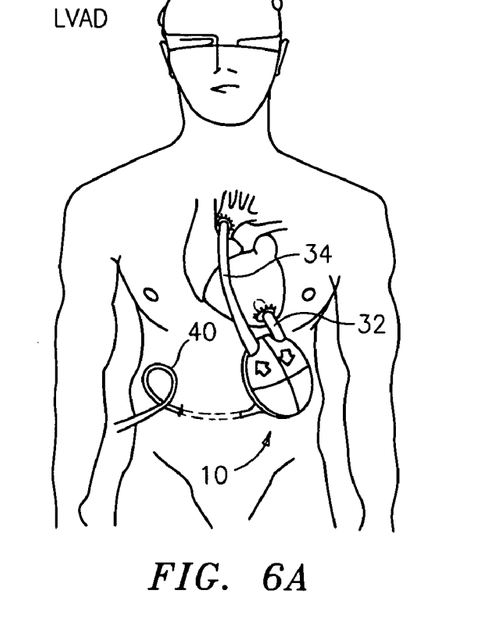
FIGS. 6A–6C show various elevation views of how the ventricular assist device is placed and connected for use with a patient.
Figure 6B:
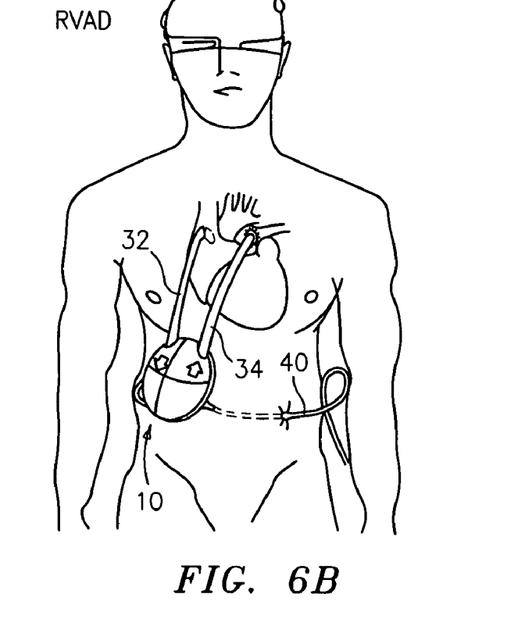
Figure 6C:
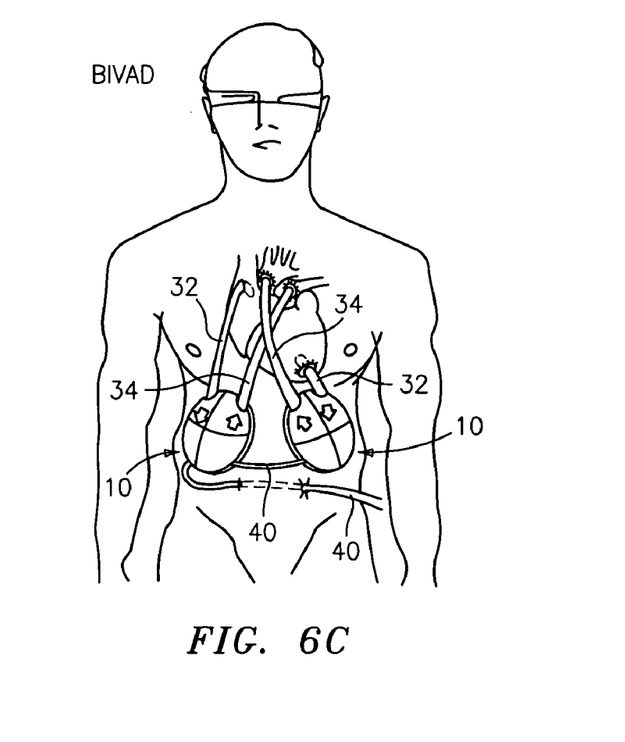

FIGS. 5A and 5B (in addition to FIGS. 1–3) show the preferred pumping sac 22. The pumping sac is bilaterally symmetric and includes circular/tubular inlets 70, 72 connected to a main pump chamber 73. The pump chamber 73 sports a gently rounded or circular profile, which has been found to maximize pumping effectiveness and to reduce blood trauma during the pumping action. More specifically, the pump chamber 73 is generally shaped like a semi-flattened ellipsoid, i.e., flat, circular top and bottom walls 74a, 74b interconnected by a rounded sidewall 75.

The blood sac, valves, and/or cannulae may be coated with lubricant, hydrophobic, antibacterial and/or antithrombotic coatings, including but not limited to PTFE coatings, heparin bonded coatings, fluorinated coatings, treclosan and silver compound coatings, and anti-calcification agent releasing coatings such as previously described to improve blood compatibility and non thrombogenicity.

The connectors 28, 30 are made of a hard material (e.g., plastic, stainless steel, titanium), molded or machined, that will secure the connection between the valves 24, 26 and the cannulae 32, 34. The tubing connectors 28, 30 each include a cylindrical through-bore, a cylindrical fore-portion that fits into the valves 24, 26, an annular flange (e.g., 76) which corresponds in shape to the pump inlet shoulders (e.g., 37), and a rear-portion dimensioned to accommodate a cannula. In use, when the pumping unit 20 is placed in the pump shell 12, the valves' annular flanges (e.g., 76) lie against the pump inlet shoulders, securely holding the tubing connectors 28, 30 in place and preventing their removal from the pump shell.

The seal 18 is made of a soft elastomer like the pumping sac and valves, but will not be in contact with blood and is only used to insure an airtight fit of the shell halves 14, 16. The disposable pumping unit 20 (i.e., blood sac, valves and connectors and seal) may be preassembled and coated as a single disposable part.

To ensure that the cannulae 32, 34 remain securely connected to the connectors 28, 30, the inlet and outlet portions 44, 46 of each pump shell half are provided with protruding, semi-annular gripping ridges 60 (see FIG. 2). In use, when the pumping unit 20 is placed in the lower shell half 16, as shown in FIG. 3, the cannulae 32, 34 contact the gripping ridges of the lower half 16. Then, when the upper half 14 is placed against and connected to the lower half 16, the gripping ridges 60 of both halves bite into and engage the cannulae, securing them in place.

Figure 7:
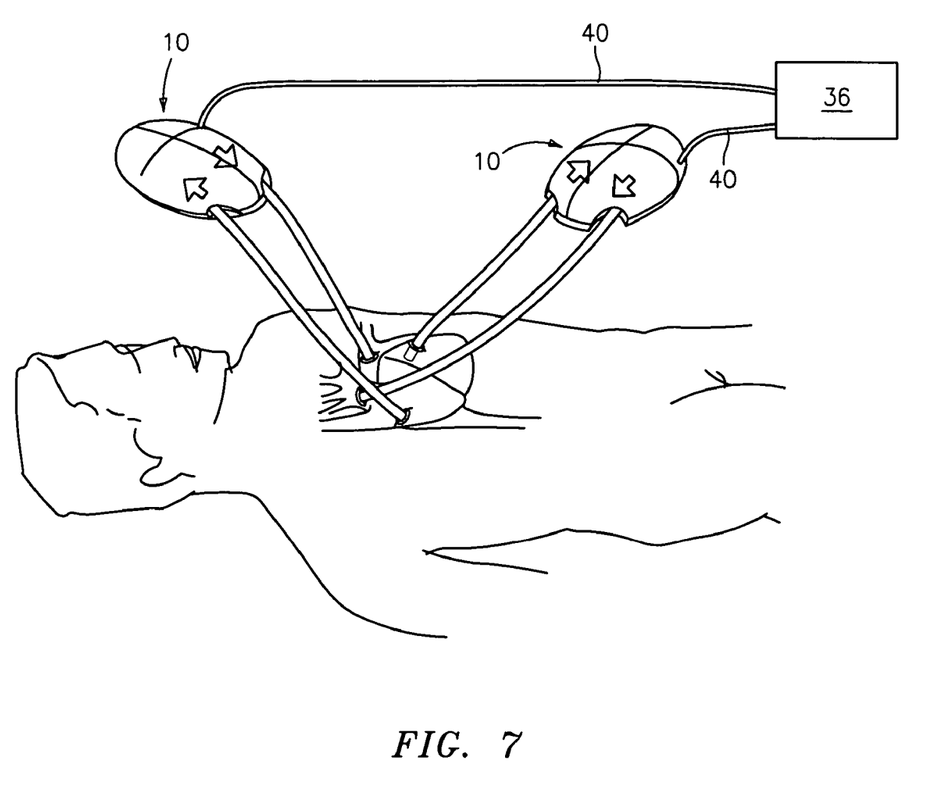
FIG. 7 is a perspective view of two of the ventricular assist devices in use extracorporeally with a patient.

The whole system has been designed to be used in a wide range of applications of circulatory support, by simply selecting the appropriate cannulae and accessories. Intended applications include short term trans-operative support (a few hours), acute and post-cardiotomy support (up to a couple of weeks), bridge to transplant (~3–6 months), bridge to recovery (~several years) and destination therapy (until death). The device is also designed to be used as either a right VAD (FIG. 6B), a left VAD (FIG. 6A), or for bi-ventricular use (FIG. 6C), and to be used as a tethered implant(s), paracorporealy, or extracorporealy (FIG. 7).

To install the system, first the cannulae are sewn to the atrium, ventricle or outflowing artery of the compromised side of the heart, as applicable. The cannulae are then connected to the disposable pumping unit 20, while carefully removing any air bubbles in the system. The blood sac assembly is supple and flexible, facilitating its priming and de-bubbling. The connectors 28, 30 are also made to be easily connected and disconnected, facilitating this procedure. Once the system has been properly purged and connected, the pumping shell 12 is locked closed over the pumping unit. The blood sac assembly is symmetrical so that it can be placed either with the inflow valve on the left or on the right, making its design more adaptable to different applications. The connectors fit inside the pumping shell so that when the latter is closed it will crimp down on the cannulae connections preventing an accidental disconnection, as mentioned above. The device can then be placed in the abdomen or outside the body and the drive unit can be activated to start pumping.

Although the ventricular assist device of the present invention has been illustrated as having a pump shell with two separate halves 14, 16, the halves could be hinged together or otherwise permanently connected without departing from the spirit and scope of the invention. Also, although the pumping unit has been described as comprising separate components connected together, the pumping unit could be provided as a single unit, i.e., a unitary piece of molded silicone. This also applies to the valves 24, 26 and connectors 28, 30, i.e., the connectors could be provided as part of the valves.

Although the valves 24, 26 have been characterized as being identical and each having two leaflets, it should be appreciated that the valves 24, 26 could have a different number of leaflets, i.e., 1 leaflet, or 3 leaflets, and the two valves 24, 26 could be different from one another. More specifically, where operating pressures on the two valves may be different (because one is acting as an inlet valve and the other acting as an outlet valve), it may be advantageous to utilize valves with different characteristics.

Since certain changes may be made in the above-described universal pneumatic ventricular assist device, without departing from the spirit and scope of the invention herein involved, it is intended that all of the subject matter of the above description or shown in the accompanying drawings shall be interpreted merely as examples illustrating the inventive concept herein and shall not be construed as limiting the invention.

Having thus described the invention, what is claimed is:
1. A pneumatic ventricular assist device for assisting in the pumping of blood to and from a heart, wherein the device comprises:
   a. a split pump housing having two housing halves that fit together to define an interior chamber with a pump inlet and a pump outlet; and
   b. a pumping unit, for pumping blood, comprising: a flexible blood sac configured to reside in the chamber and having a sac inlet and a sac outlet; first and second one-way valves, not integral with the blood sac, dimensioned to fit in the pump inlet and pump outlet, respectively connected to the sac inlet and sac outlet, wherein the first and second one-way valves are one-piece, hinge-less valves each having a valve inlet side, a valve outlet side, and a pair of flexible valve leaflet portions separating the valve inlet and outlet sides, wherein each pair of the leaflet portions:
      i. defines a channel between the adjacent leaflets that is normally open in the absence of any compressive force;
      ii. compress together, preventing blood from flowing back through the valve, when blood pressure is greater on the valve outlet side than on the valve inlet side; and
      iii. flex outwards, allowing blood to pass through the valve, when blood pressure is greater on the valve inlet side than on the valve outlet side.

2. The pneumatic ventricular assist device of claim 1 wherein first and second tubing connectors, extending through the pumping shell pump inlet and pump outlet, respectively connect the first and second valves to the exterior of the housing, and the pump inlet and pump outlet each include an annular, inwards-facing shoulder against which annular flange portions of the tubing connectors respectively rest to hold the tubing connectors in place.

3. The pneumatic ventricular assist device of claim 1 wherein the pump housing has a rounded, generally-flattened, ellipsoid-shaped outer surface for facilitating implantation.

4. A pneumatic ventricular assist device for assisting in the pumping of blood to and from a heart, wherein the device comprises:
   a. a pump shell having an interior chamber with a pump inlet and pump outlet leading to an exterior of the shell; and
   b. a pumping unit comprising: a flexible blood sac configured to reside in the interior chamber and having a sac inlet and a sac outlet; first and second hingeless one-way valves, not integral with the blood sac, dimensioned to fit respectively in the shell pump inlet and pump outlet respectively connected to the sac inlet and a sac outlet, wherein the one-way valves comprise:
      i. a cantilevered pair of adjacent tapered ledges, with distal ends, that resemble the head of needle-nose pliers;
      ii. the ledges define a channel between them that is normally opened, in the absence of compressive forces, to permit a one-way flow of blood from the sac to the pump outlet; and
      iii. an opposite blood flow compresses the distal ends together, thereby closing off the channel between them and blocking the flow of blood.

5. The pneumatic ventricular assist device of claim 4 wherein the device further includes: (i) first and second tubing connectors, extending through the pump inlet and pump outlet, respectively connect the first and second valves to the exterior of the shell, and the pump inlet and pump outlet each include an annular, inwards-facing shoulder against which annular flange portions of the tubing connectors respectively rest to hold the tubing connectors in place; and (ii) the pump inlet and pump outlet each include an annular gripping ridge for securing cannulae connected to the tubing connectors in place when the pumping shell halves are connected together.

6. The pneumatic ventricular assist device of claim 4 wherein the shell has a rounded, generally-flattened, ellipsoid-shaped outer surface for facilitating implantation.

* * * * *